(12) United States Patent
Rikimaru (10) Patent No.: US 7,421,392 B2
(45) Date of Patent: Sep. 2, 2008

(54) DIAGNOSIS DEVICE AND DIAGNOSIS METHOD

(75) Inventor: Hiroshi Rikimaru, Kyoto (JP)

(73) Assignee: RION Co., Ltd., Tokyo (JP)

( * ) Notice: Subject to any disclaimer, the term of this patent is extended or adjusted under 35 U.S.C. 154(b) by 258 days.

(21) Appl. No.: 10/538,480

(22) PCT Filed: Dec. 9, 2003

(86) PCT No.: PCT/JP03/15751

§ 371 (c)(1),
(2), (4) Date: Jun. 7, 2005

(87) PCT Pub. No.: WO2004/056272

PCT Pub. Date: Jul. 8, 2004

(65) Prior Publication Data

US 2006/0167681 A1    Jul. 27, 2006

(51) Int. Cl.
G10L 11/00 (2006.01)
G10L 21/00 (2006.01)
G09B 19/04 (2006.01)

(52) U.S. Cl. ................ 704/271; 704/226; 434/185

(58) Field of Classification Search ............ None
See application file for complete search history.

(56) References Cited

U.S. PATENT DOCUMENTS

| | | | |
|---|---|---|---|
| 3,784,750 A | | 1/1974 | Stearns et al. |
| 5,303,327 A | * | 4/1994 | Sturner et al. ............. 704/270 |
| 5,813,862 A | * | 9/1998 | Merzenich et al. .......... 434/185 |
| 6,109,107 A | * | 8/2000 | Wright et al. ............... 73/585 |
| 6,334,776 B1 | * | 1/2002 | Jenkins et al. ............. 434/169 |
| 6,584,440 B2 | * | 6/2003 | Litovsky ................... 704/271 |
| 7,110,951 B1 | * | 9/2006 | Lemelson et al. .......... 704/270 |

FOREIGN PATENT DOCUMENTS

| | | |
|---|---|---|
| JP | 01-163873 A | 6/1989 |
| JP | 2000-139856 A | 5/2000 |
| JP | 2001-314376 A | 11/2001 |
| JP | 2001-331581 | 11/2001 |
| JP | 2002-169885 A | 6/2002 |
| JP | 2002-306492 A | 10/2002 |

OTHER PUBLICATIONS

Robert V. Shannon et al., "Speech Recognition with Primarily Temporal Cues", Science, vol. 270, pp. 303-304, House Ear Institute (Oct. 13, 1995).

(Continued)

Primary Examiner—David R. Hudspeth
Assistant Examiner—Matthew J. Sked
(74) Attorney, Agent, or Firm—Rader, Fishman & Grauer, PLLC (57) ABSTRACT

The present invention provides a diagnostic device that presents, to a patient, a Noise-Vocoded Speech Sound signal that is obtained by dividing at least one portion of a sound signal into a single or a plurality of frequency band signals and subjecting the frequency band signals to noise, and analyzing the content of a response recognized by the patient and the presented stimulus to diagnose a disease of the patient based on the analysis results, so that diagnosis including determining the disease of the patient and estimating a damaged site can be performed.

9 Claims, 6 Drawing Sheets

OTHER PUBLICATIONS

Yoshihisa Obata et al., "Speech perception based on temporal amplitude change with spectrally degraded synthetic sound", Transaction of the Technical Committee on Psychological and Physiological Acoustics, H-99-6, pp. 1-8, Acoustical Society of Japan (Jan. 29, 1999).

Yoshihisa Obata et al., "Intelligibility of synthesized Japanese speech sound made of band noise preliminary study for a speech recognition processor utilizing central auditory function", Transaction of the Technical Committee on Psychological and Physiological Acoustics, H-2000-3, pp. 1-8, Acoustical Society of Japan (Jan. 28, 2000).

International Search Report mailed on Jan. 20, 2004.

First Office Action from State Intellectual Property Office of People's Republic of China dated Jul. 27, 2007 for application No. 200380105369.9 w/ Chinese translation.

Wang Yin-hua, "A distinguishing and diagnosing process of aphasiac types in Chinese aphasia (2)", Theory and Practice in Chinese Rehabilitation, vol. 3, No. 2, pp. 57-59, 1997.

Office Action from Japanese Patent Office for application No. 2002-367779 dated Apr. 9, 2008.

Kondo et al., "Initial Evaluation of a Novel Japanese Intelligibility Test", The Institute of Electronics; Technical Report of IEICE, SP 2000-163, pp. 25-33.

* cited by examiner

DIAGNOSIS DEVICE AND DIAGNOSIS METHOD

TECHNICAL FIELD

The present invention relates to a diagnostic device that employ Noise-Vocoded Speech Sound obtained by subjecting at least one frequency band signal of a sound signal to noise and a method thereof. In particular, the present invention relates to devices and methods suitable for diagnosis of a patient who might suffer from a neural disorder.

BACKGROUND ART

Conventionally, a diagnosis to a patient who might have had cerebral infarction, cerebral hemorrhage or the like is performed, using a X-ray computerized tomography system, a MRI (magnetic resonance image) tomography system, a positron emission tomography system utilizing positron emission or the like.

On the other hand, in research on recognition of sound signals, it has come to be known that a speech can be recognized to a considerable extent without hearing a complete sound signal, that is, even if a component of a sound signal is subjected to noise by a certain method. Such a technique is disclosed in, for example, reference 1 (Shannon, R. V., et. al, "Speech Recognition with Primarily Temporal Cues", SCIENCE, 1995, no. 270, pp. 303 to 305), reference 2 (an article of an auditory sense study group of Acoustical Society of Japan, "Speech perception based on temporal amplitude change with spectrally degraded synthetic sound" by Yoshihisa Obata and Hiroshi Rikimaru, 1999, H-99-6), reference 3 (an article of an auditory sense study group of Acoustical Society of Japan, "Intelligibility of synthesized Japanese speech sound made of band noise—preliminary study for a speech recognition processor utilizing central auditory function—" by Yoshihisa Obata and Hiroshi Rikimaru, 2000, H-2000-3).

According to such references, a sound signal is divided into four frequency bands (0 to 600, 600 to 1500, 1500 to 2500, 2500 to 4000 Hz), each sound signal is subjected to half-wave rectification and is applied to a 16 Hz lowpass filter so as to obtain an amplitude envelope of each frequency band, and is multiplied by a band noise corresponding to each frequency band, and the thus obtained signals are added to generate a signal. Such a signal is referred to as "Noise-Vocoded Speech Sound". It has been reported that when people with normal hearing ability heard the Noise-Vocoded Speech Sound, an intelligibility of about 80% was obtained.

Conventionally, X-ray computerized tomography systems, MRI (magnetic resonance image) tomography systems, positron emission tomography systems utilizing positron emission and the like have been used to diagnose a disease of a patient who might suffer from a neural disorder stemming from cerebral infarction, cerebral hemorrhage or the like. Although the use of these systems is an effective approach to detect an injured part or a focal part, this approach is an anatomical diagnosis of a disordered site and has a difficulty in diagnosing the function. If there is a simple method for diagnosing the function that cannot be clarified only by anatomical images without using a large scale device, such a method can achieve easy diagnosis. Furthermore, there is also a demand for diagnostic devices for a disorder such as presbycusis, congenital deafness, hearing impairment with independent of the neural disorder.

DISCLOSURE OF THE INVENTION

In order to solve the above-described problems, the diagnostic device of the present invention adopts the following means and approaches.

(1) The present invention provides a diagnostic device for diagnosing a disease of a patient by presenting, to a patient, a Noise-Vocoded Speech Sound signal obtained by dividing at least one portion of a sound signal into a single or a plurality of frequency band signals and subjecting the frequency band signals to noise; analyzing a content of a response recognized by the patient and the presented stimulus; and diagnosing the disease of the patient based on the results of the analysis. This is useful to determine the disease of the patient and to estimate the injured site.

(2) The Noise-Vocoded Speech Sound signal in which a component of a sound source signal is subjected to noise is generated by extracting a frequency band signal with a predetermined frequency band from at least one portion of the sound source signal by a first band filtering procedure having a plurality of band filtering procedures; extracting an amplitude envelope of each frequency band signal by an envelope extracting procedure; generating a frequency band noise signal corresponding to the predetermined frequency band from a noise source signal by a second band filtering procedure having a plurality of band filtering procedures; multiplying the frequency band signal and the frequency band noise signal in a multiplying procedure; and accumulating outputs obtained by the multiplying procedure in an adding procedure. If the number of band filters or the frequency boundary of the frequency bands can be selected or changed, the present invention can be used for various diagnostic purposes. Furthermore, with automatic language recognition, when the number of band filters or the frequency boundary of the frequency bands is selected or changed suitably with a language, the present invention can be used by a plurality of peoples with different nationalities, and can be used for diagnosis of people from abroad.

(3) The above-described diagnostic device can be implemented with the procedures of a computer program or the like, and therefore can be made into a recording medium storing a program that is executed by a computer or a program that is executed by a computer.

BEST MODE FOR CARRYING OUT THE INVENTION

Hereinafter, embodiments of the diagnostic device will be described with reference to the accompanying drawings. It should be noted that components bearing the same reference numeral in the embodiments perform the same operation and may not be described in duplicate.

Embodiment 1

Figure 1:
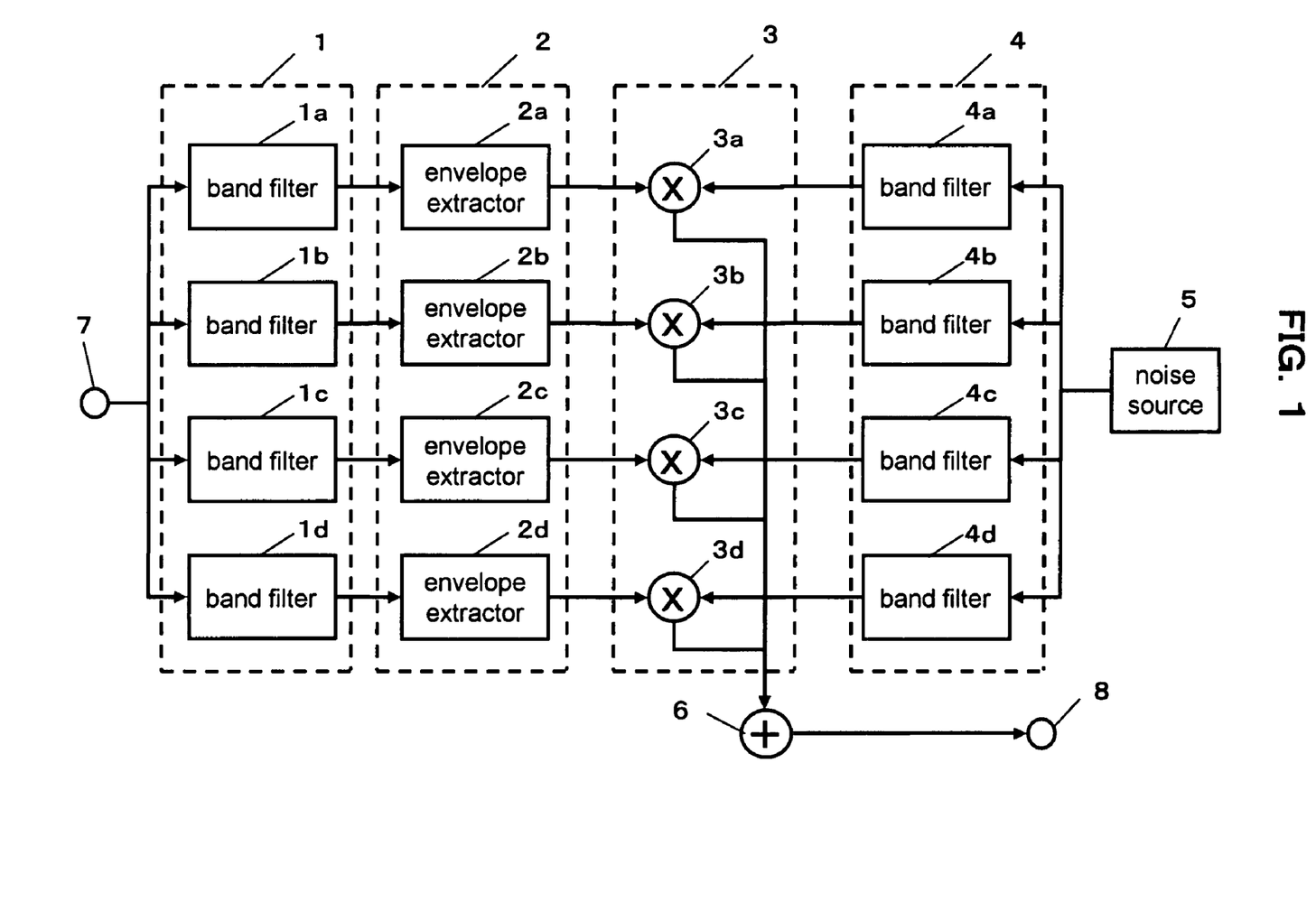
FIG. 1 is a block diagram of a Noise Vocoded Speech Sound converting portion used in one embodiment of the present invention.

First, a method for generating the Noise Vocoded Speech Sound and an effect of diagnosis therewith will be described. FIG. 1 is a block diagram of a Noise Vocoded Speech Sound converting portion used in the present invention. In FIG. 1, a sound signal is applied to a band filtering portion 1 via an input terminal 7. The band filtering portion 1 has a plurality of band filters 1a, 1b, 1c and 1d for extracting signals having a predetermined frequency band. Output signals from the band filters 1a, 1b, 1c and 1d are applied to envelope extractors 2a, 2b, 2c and 2d, respectively, of an envelope extracting portion 2 so that the amplitude envelope of each frequency band signal is extracted. A noise signal output from a noise source 5 is applied to a band filtering portion 4 having a plurality of band filters 4a, 4b, 4c and 4d, to be divided into noise signals having the same frequency bands as those of the band filtering portion 1. The outputs from the envelope extractors 2a, 2b, 2c and 2d and the outputs from the band filters 4a, 4b, 4c and 4d are multiplied for each corresponding band in a multiplying portion 3 having multipliers 3a, 3b, 3c and 3d. The multiplied results are summed up in an adding portion 6, and then become output signals in an output terminal 8.

When a patient was let to hear the Noise Vocoded Speech Sound that is generated in this manner and recognized words or sentences are examined, then it was found that there are characteristics in the recognition results, depending on the disease of the patient. There are differences in the recognition results between disorders such as cerebral infarction, cerebral hemorrhage, presbycusis, congenital deafness, hearing impairment with independent of the neural disorder. It is estimated that a neural function or a neural site used when hearing and recognizing a sound signal that has been converted to a Noise Vocoded Speech Sound is different from when hearing and recognizing an ordinary speech sound, so that the recognition results are unique to each disease. By combining the present invention with MR images or the like as necessary, this phenomenon is utilized for highly accurate diagnosis.

Figure 2:
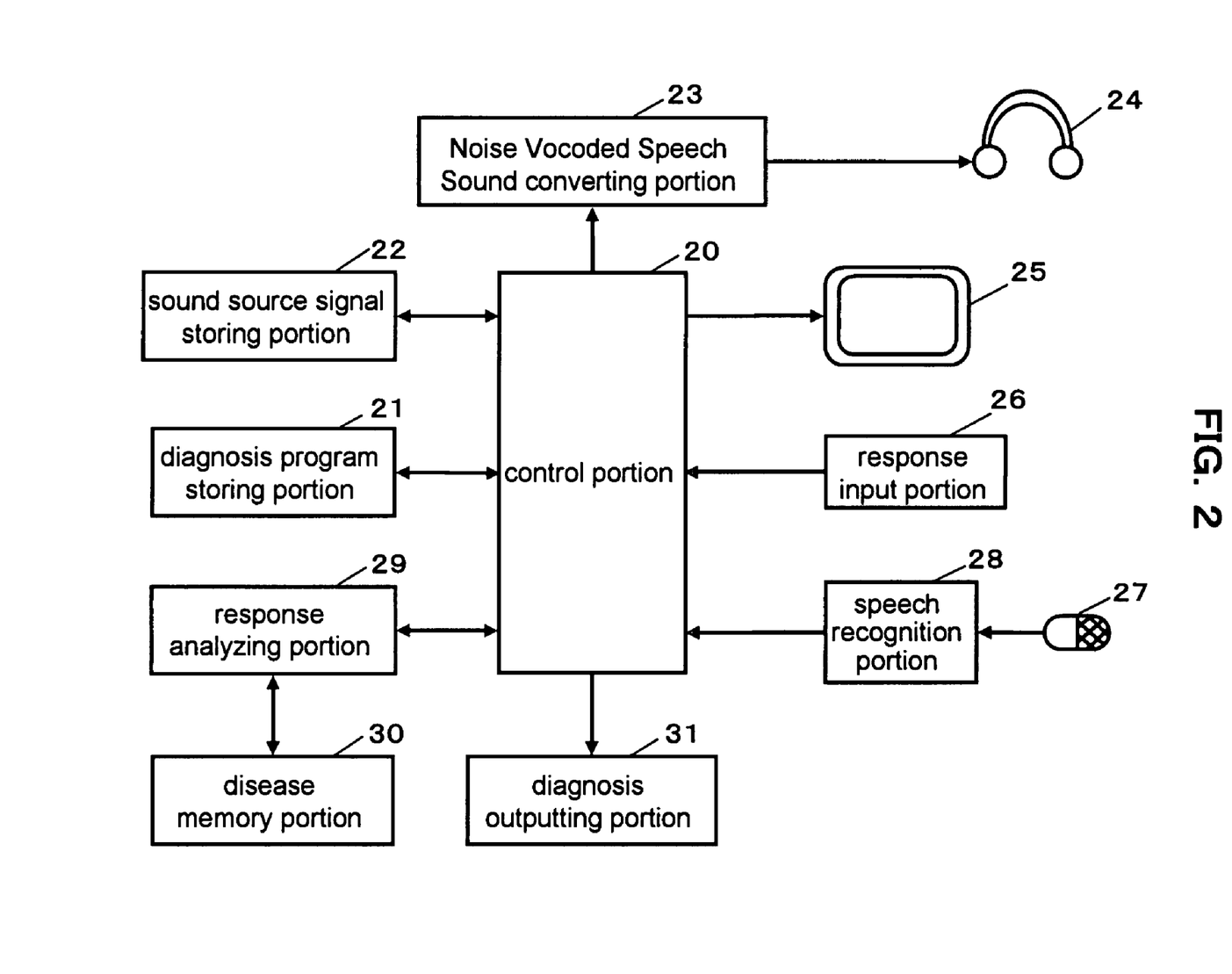
FIG. 2 is a block diagram of a diagnostic device according to one embodiment of the present invention.

FIG. 2 is a block diagram of the diagnostic device using the Noise-Vocoded Speech Sound of the present invention. The configuration will be described with reference to FIG. 2. A diagnosis program is contained in a diagnosis program storing portion 21. The diagnosis program refers to a program including a series of procedures, for example, in which five stimuli, each of which is constituted by a word or sentence, constitute one set, and the stimuli are presented sequentially one by one, five words or sentences that are recognized when a patient listened to the Noise Vocoded Speech Sounds thereof are obtained as recognition results, and the disease of the patient is estimated from the recognition results. The number of stimuli is not limited to 5, and at least one is sufficient. The diagnosis program stores the identification codes of the five stimuli that are to be presented to a patient and the procedure for presenting the same, and also stores data for displaying diagnosis procedure and instructions to a patient. A sound source signal storing portion 22 stores sound signals of various words and sentences for diagnosis that make a pair with the identification codes. A Noise Vocoded Speech Sound converting portion 23 is an element described with reference to FIG. 1, and converts a sound signal input from a control portion 20 to a Noise Vocoded Speech Sound signal, which is applied to a headphone 24 so that a patient can hear the Noise Vocoded Speech Sound through the headphone 24. A display portion 25 displays data for explanation or instructions for patients supplied from the control portion 20 with texts or graphics on the screen. A response input portion 26 is a keyboard with which a word or sentence that is recognized when a patient listened to a Noise Vocoded Speech Sound. The input reaction enters the control portion 20. A microphone 27 and a speech recognition device 28 recognize a response or reaction made of speech sounds of the patient, and the response or reaction enters the control portion 20. A response analyzing portion 29 analyzes the contents of collected responses and compares the analysis results with disease database of a disease memory portion 30 to estimate the disease. A diagnosis output portion 31 outputs diagnosis results, and can be a printer or a display.

Next, the operation of the diagnostic device of the present invention will be described.

Upon detection of an instruction to start diagnosis with a starting button, the control portion 20 reads out a diagnosis program from the diagnosis program storing portion 21 and sends data for explanation and instructions for patients to the display portion 25 and lets it display the data. Then, the control portion 20 reads out the identification code of a sound source signal to be presented from the diagnosis program, reads out speed sound signals of a designated word or sentence from the sound source signal portion 22, based on the identification code, and applies it to the Noise Vocoded Speech Sound converting portion 23. The Noise Vocoded Speech Sound converting portion 23 converts the sound signals to Noise Vocoded Speech Sound, which are presented to a patient through the headphone 24. The patient inputs the recognized word or sentence when listening to a presented a stimulus to the keyboard of the response input portion 26. When it is difficult for the patient to input by himself, for example, due to damages incurred by the patient, an examiner or a diagnostician listens to or looks at an answer or reaction of the patient and then inputs. The control portion 20 captures and stores the input response data. The control 20 has obtained a response to a presented stimulus, and therefore reads out instruction data to be presented next and the identification code of the sound source signals from the diagnosis program in the diagnosis program storing portion 21, lets the instruction data displayed, lets a stimulus presented, and captures and stores response data by the same procedure as above, and then proceeds with the next stimulus presentation. In this manner, the control portion 20 sends to five sets of response data that are obtained corresponding to the five stimuli to the response analyzing portion 29. The response analyzing portion 29 analyzes the response content, using disease database that are stored in the disease memory portion 30, estimates the disease, and sends the estimated disease data to the control portion 20. The control portion 20 outputs the estimated disease name and the disease data from the diagnosis output portion 31.

Next, the mechanism of the diagnosis will be described by taking an example. Herein, a case of diagnosis of a disease from four diseases, using two sentences as stimuli will be described. A sentence "a-me-ga-fu-ru (which means it rains)" is taken as a first stimulus sentence A0. It is assumed that a patient P1 listened to the Noise Vocoded Speech Sound signals of this sentence and gave a response sentence A1 "a-re-ga-ku-ru". When A0 is compared with A1, "me" and "fu" are recognized as "re" and "ku", respectively. The vowel sounds are correct, but the consonants are incorrect. The manner of making an error depends on the disease, and response sentences A1, A2, and A3 are obtained, corresponding to three diseases.

There are response sentences B1 to B3 as a result of recognition of a second stimulus sentence B0 "kyo-u-ha-sa-mu-i" (which means that it is cold today).

In the disease database, a correspondence table is stored in which a corresponding disease of four diseases is allocated to each of 9 combinations of the response sentences Ai (i=1 to 3) to the stimulus sentence A0 and the response sentences Bj (j=1 to 3) to the stimulus sentence B0. The response analyzing portion 29 searches the disease database based on the obtained responses Ai and Bj, and obtains a disease name Sk (k=1 to 4) corresponding to {Ai, Bj}.

The above example is an example in which four diseases can be identified distinctly by searching for a disease name, using responses to the two stimulus sentences as an input function. The format of the disease database is not limited to the one in the above example.

A variation pair of the stimulus sound and the response sound by the unit of syllable, mora, sound or the like that was an error in each stimulus sentence may be analyzed in the replay analyzing portion 29, and a set of such variation pairs may be input in the disease database as an input function to search for a disease name. The disease database stores linkage between names of diseases and sets of variation pairs in the form of a polyvalent function. The input function may include stimulus sentences or identification codes thereof.

As an element of the input function, a stimulus sentence, a response sentence, a presented sound (correct sound) and a response sound (incorrect sound) in each sentence can be used. As the unit of sounds, the syllable unit, the mora unit, the consonant unit, the vowel unit or the like can be used. Furthermore, the correlation between the element as described above and disease name may be represented by a numeral value, the sum of correlation values with respect to the input function or a comprehensive correlation value may be obtained, and a plurality of disease names may be selected, starting from the disease name having the largest correlation value and may be output together with the correlation values.

The disease database can be generated by a method in which doctors, speech therapists, audiologists analyze diagnosis results of a large number of patients from their experiences, collect responses with respect to stimulus sentences of a suitable population of patients, and performs factor analysis of the results.

When responses unique to a specific disease can be obtained with specific sentences with sound signals that are not be converted to Noise Vocoded Speech Sounds, such sentences can be incorporated in the diagnosis program and incorporated in the database structure.

Embodiment 2

In the above description, the diagnosis program can proceed sequentially step by step to supply five stimuli. However, the diagnosis program can be divided into two steps, and in the first step, a basic diagnosis is performed, and then, based on the results, the program moves to the second step for detailed diagnosis. In this case, when the response analyzing portion 29 sends the results of the basic diagnosis to the control portion 20, the control portion 20 selects one from a plurality of prepared diagnosis programs for the second step, based on the results, and moves the diagnosis to the second step.

Embodiment 3

A patient may input from the microphone 27 with voice, instead of inputting from the keyboard, and the voice may be converted to text information by the speech recognition portion 28 and be input to the control portion 20.

Embodiment 4

For the frequency bands of the band filters of the band filtering portions 1 and 4 of the Noise Vocoded Speech Sound converting portion 23, 0 to 600 Hz, 600 to 1500 Hz, 1500 to 2500 Hz, and 2500 to 4000 Hz are used as the standard frequency bands. As in the Noise Vocoded Speech Sound shown in FIG. 3, a band selecting portion 12 may be provided to switch the above-described frequency bands of the band filtering portions 1 and 4. For example, the number of frequency bands can be selected among 1, 2, 3, and 4. This is because there is a case in which the four frequency bands are not necessary, depending on the words, or the condition of vowel sounds or consonants. For example, the number of the frequency bands can be 2 by setting the output from the band filters 1c, 1d, 4c and 4d to 0. Furthermore, with respect to all or any part of the band filters, the boundary frequency defining the frequency bands can be switched to other frequencies than 600 Hz, 1500 Hz, 2500 Hz, and 4000 Hz. 600 Hz, 1500 Hz, 2500 Hz, and 4000 Hz are close to the standard frequency boundary that separates the vowel sounds of sound, that is, /a/, /i/, /u/, /e/, and /o/ in Japanese by the first and the second formants. However, the frequency boundary may be slightly different from person to person. An accurate diagnosis may be obtained by adjusting and changing the boundary of the frequency bands in accordance with such a difference between individuals, so that the device is configured such that the boundary can be switched and selected. The number of the frequency boundary may be larger than 4. Furthermore, foreign languages have a vowel system different from that of Japanese, so that the device may be configured such that the number of the band filters or the boundary frequency can be switched in order to be used with foreign languages.

The number of the band filters or the number of the frequency boundary may be changed according to the diagnosis program, or may be changed in connection with the disease database.

The microphone may be connected to the control portion 20, and doctors, speech therapists, audiologists or the like may present words or sentences that are not included in the sound source signal storing portion 22 as a stimulus. In this case, ambient noise may be mixed from the microphone, so that, as in the Noise Vocoded Speech Sound converting portion 23 shown in FIG. 3, the sound signal extracting portion 9 is provided, and only sound components are extracted from input sound signals and applied to the band filtering portion 1. In order to extract the sound components, the configuration may be such that ambient noise other than speech sound components contained in the input sound signals is suppressed by, for example, a spectrum subtraction technique.

Figure 3:
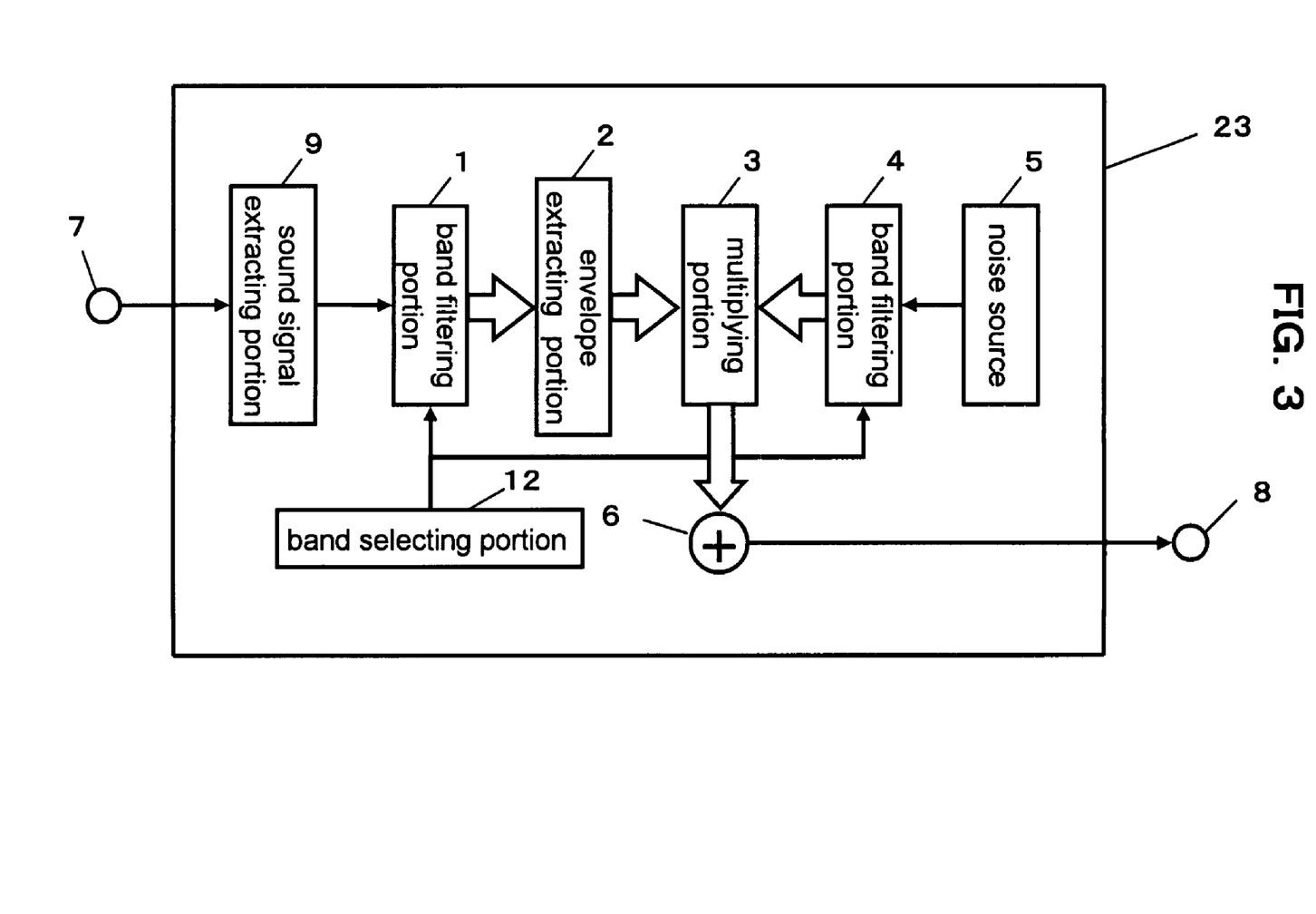
FIG. 3 is a block diagram of a Noise Vocoded Speech Sound converting portion used in one embodiment of the present invention.

For use with foreign languages, a language automatic recognition portion may be provided, and words or sentences that have been input first by a patient or a trainer through the microphone 27 may be automatically recognized by the speech recognizing portion 28. Then, the band selecting portion 12 may set the number of the band filters and the frequency band boundary corresponding to the language of the country in the band filtering portion 1 and 4, sound signals with the language of the country may be used, and the disease database corresponding to the language of the country may be used.

In order to determine the boundary frequency of the frequency bands, the frequency characteristics of the language of the pronounced speech are analyzed, a change of the primary peak of the frequency component is observed over time, and movement of each formant is detected from the pattern of this change, so that the boundary frequency can be determined. In this manner, the boundary frequency that matches the characteristics of the pronounced speech of a diagnostician, that is, an examiner can be used. The Noise Vocoded Speech Sound conversion may be performed while determining the boundary frequency in real-time. Also in the case where a boundary frequency corresponding to a foreign language is used, such a technique for determining a boundary frequency can be used.

Embodiment 5

Signals obtained by converting sound signals to Noise-Vocoded Speech Sounds may be previously stored in the sound source signal storing portion 22 of the diagnostic device of FIG. 2, and a patient may listen to an output signal therefrom through the headphone 24. In this case, the Noise Vocoded Speech Sound converting portion 23 may not be provided.

Embodiment 6

Figure 6:
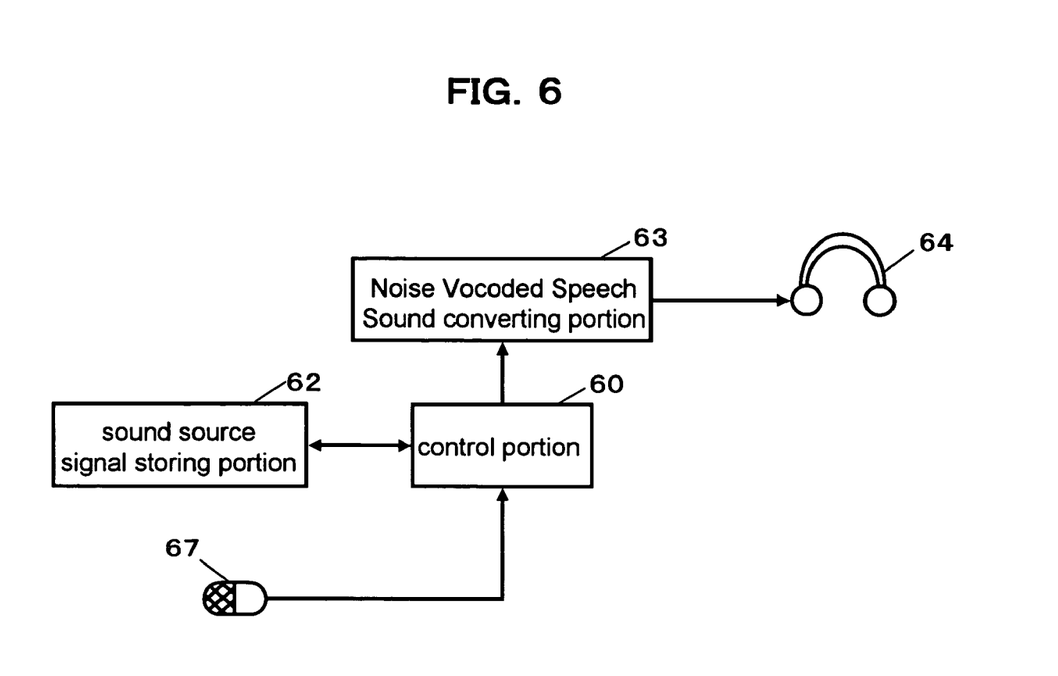
FIG. 6 is a block diagram of a diagnostic device according to one embodiment of the present invention.

FIG. 6 is a block diagram of a schematic diagnostic device. In FIG. 6, a sound source signal storing portion 62 stores sound signal data of words and sentences for stimulus presentation. When a diagnostician presses a push button(not shown), a control portion 60 reads out sound signal data from the sound source storing portion 62, and applies the same to the Noise Vocoded Speech Sound converting portion 63. The Noise Vocoded Speech Sound converting portion 63 presents the converted Noise Vocoded Speech Sound signal to a patient through a headphone 63. The patient pronounces a recognized word or sentence as a response to the diagnostician. The diagnostician writes down the response and estimates the disease from the response results. The diagnostician may pronounce a word or a sentence for presentation through a microphone 67, and the control portion 60 may present the sound data to the patient through the Noise Vocoded Speech Sound converting portion 63 and the headphone 64. In this case, as described in Embodiment 4, as a method for determining the boundary frequency of the frequency bands, the following method can be used: the frequency characteristics of pronounced speech are analyzed, a change of the primary peak of the frequency component is observed over time, and movement of each formant is detected from the pattern of this change so that the boundary frequency can be determined. In this manner, the boundary frequency that matches the characteristics of the pronounced speech of a diagnostician, that is, an examiner can be used.

When a diagnostician orally instructs a patient through the microphone 67, a transmission path may be provided to bypass the Noise Vocoded Speech Sound converting portion 63. When Noise Vocoded Speech Sound signals are stored in the sound source signal storing portion 62, the Noise Vocoded Speech Sound converting portion 63 may be omitted.

Embodiment 7

Figure 4:
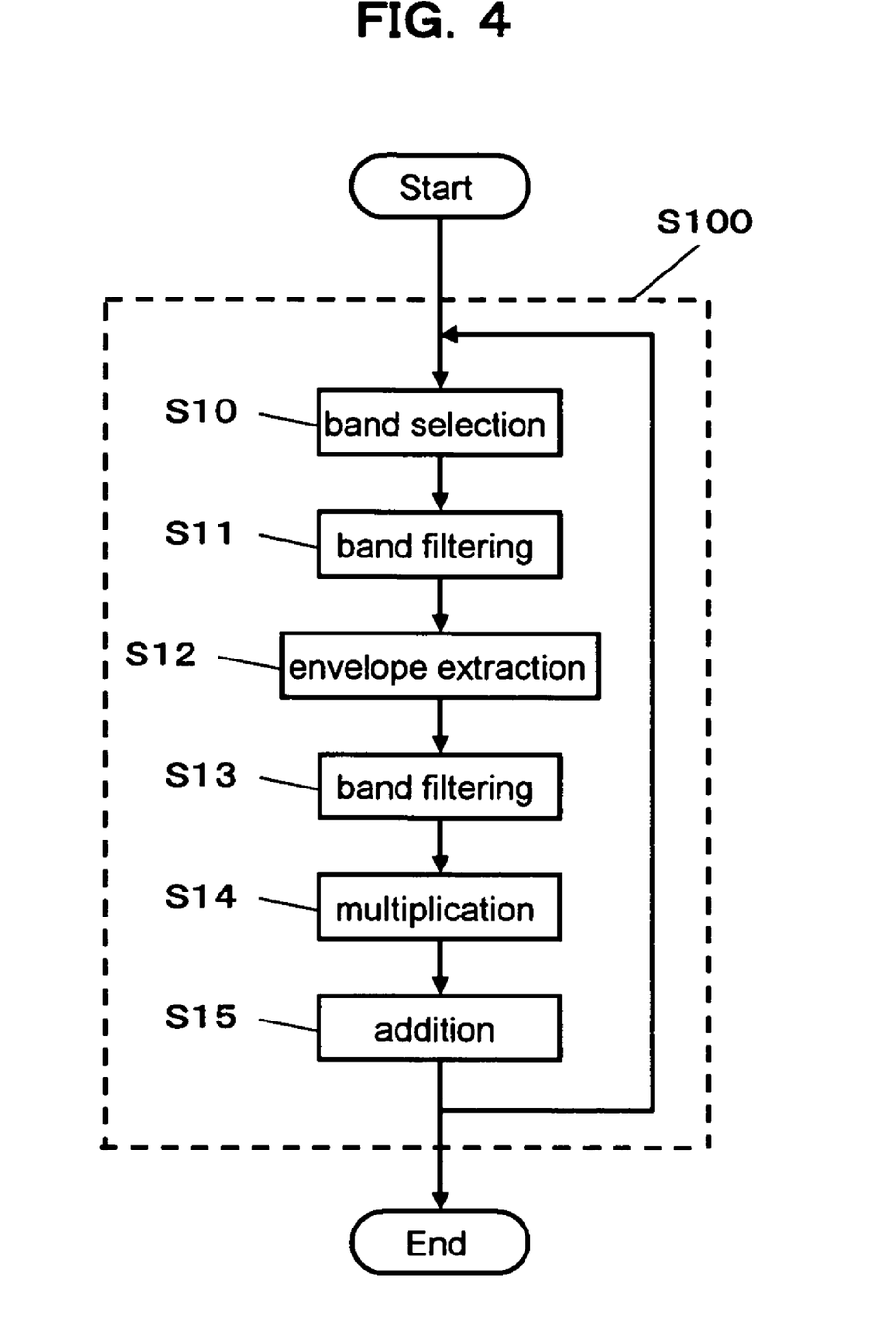
FIG. 4 is a flowchart showing the operation of a Noise Vocoded Speech Sound converting portion according to one embodiment of the present invention.

Hereinafter, an embodiment of the diagnostic method will be described. First, a method for conversion into the Noise Vocoded Speech Sound will be described. FIG. 4 is an example of a flowchart of the Noise Vocoded Speech Sound conversion. The Noise-Vocoded Speech Sound conversion procedure (S100) is constituted by steps (S10) to (S15).

First, in the band selection procedure (S10), the number of the band frequencies or the boundary frequencies of the band frequencies for band filtering that is performed in the band filtering procedures (S11) and (S13) below is changed or set, if necessary. This procedure is performed in response to an operation by a diagnostician or by an instruction from the diagnosis program. If there is no such an operation or instruction, this procedure is omitted. Next, in the band filtering procedure (S11), input sound data is filtered, based on the number of the band frequencies or the boundary frequency of the band frequencies of the band filtering that are set, to obtain band sound data. In the envelope extraction procedure (S12), from the filtered sound data, the envelope component data thereof is extracted. Then, in the band filtering procedure (S13), noise signals of white noise are filtered, according to the number of the band frequencies or the boundary frequencies of the band frequencies for band filtering that are set, so that band noise signal data is generated. The envelope component data and the band noise signal data are multiplied in the following multiplication procedure (S14), and when the multiplication results are obtained for a plurality of frequency bands, they are accumulated in the adding procedure (S15). The accumulated sound data is Noise-Vocoded Speech Sound data. This is presented to the patient through the headphone in the form of a DA-converted analog sound signal.

The steps (S10) to (S15) may be performed sequentially according to FIG. 4, or may be performed in parallel. These procedures can be realized in the form of a program of a digital signal processor (DSP).

Figure 5:
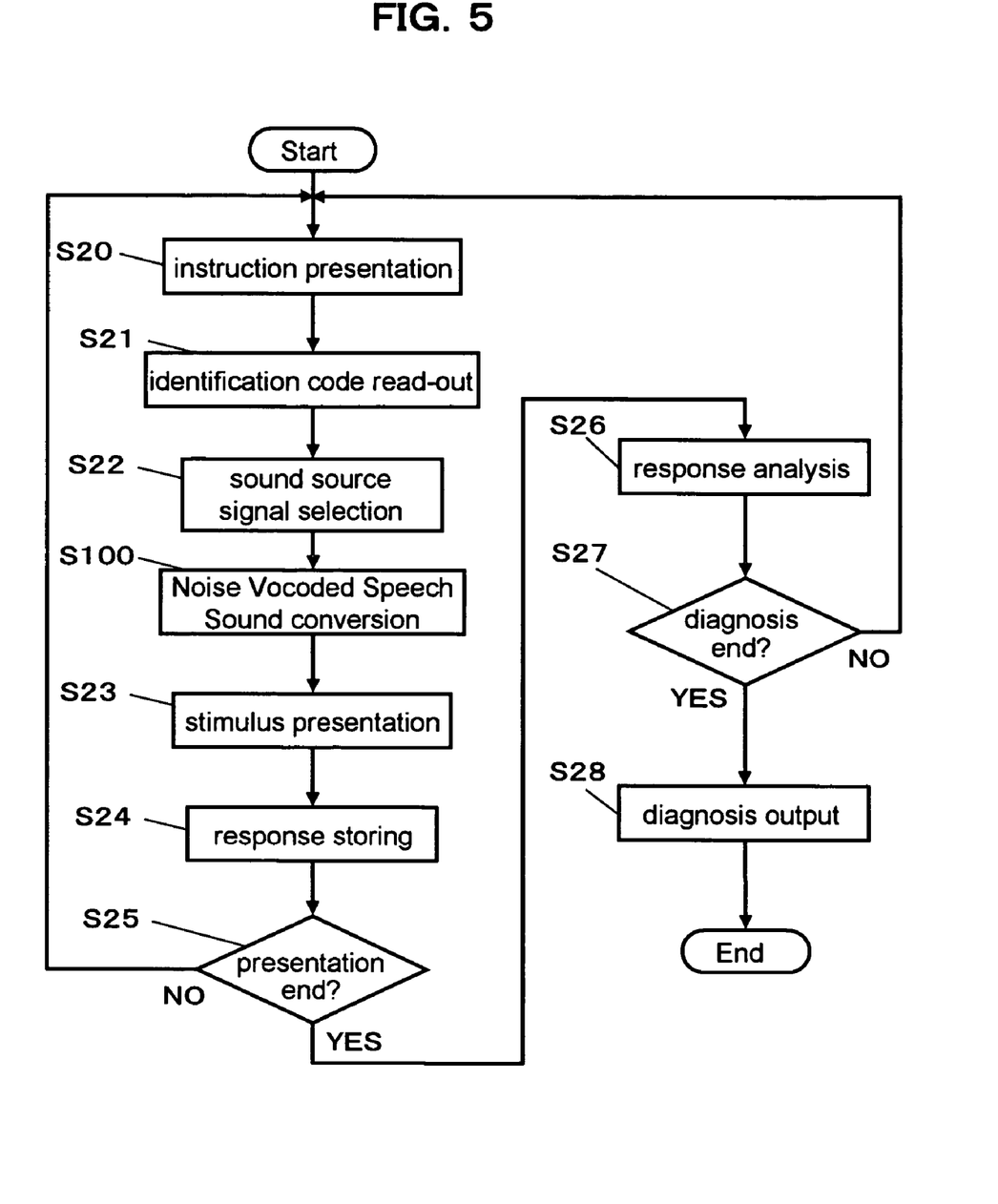
FIG. 5 is a flowchart showing the operation of a diagnostic device according to one embodiment of the present invention.

Next, an embodiment of a diagnostic method will be described. FIG. 5 is an example of a flowchart of the procedures that realize the functions of the diagnostic device of the present invention.

When a diagnosis program is started, in an instruction presentation procedure (S20), instruction information to the patient is read out from the diagnosis program and displayed in the display device 25. Then, in an identification code reading procedure (S21), the identification code of sound signals of a word or sentence to be presented is read out from the diagnosis program. In a sound signal selection procedure (S22), the sound signals of the word or sentence are selected and read out from the sound source signal storing portion 22, according to the identification code. The read-out sound signals are converted to the Noise Vocoded Speech Sound data in the Noise Vocoded Speech Sound conversion procedure (S100) as described above. Then, in a stimulus presentation procedure (S23), the Noise Vocoded Speech Sound data is converted to analog sound signal and presented to the patient as a stimulus through the headphone. When the patient listens to the Noise Vocoded Speech Sound and inputs recognized contents, the diagnostic device stores the input response data in a response storing procedure (S24). In an end determination procedure (S25), it is confirmed, referring to the diagnosis program, whether or not the presentation of a series of stimuli has ended, and if the result is NO, the procedure goes back to (S20), and moves to the next stimulus presentation. This procedure is repeated so that a set of diagnosis program menus made of a series of questions can be executed. In the end determination procedure (S25), if the result is Yes, this means that a test made of a set of stimulus series is completed, and therefore the procedure moves to (S26). Here, the disease of the patient is determined or an intermediate determination is made, based on the response results and the disease database. As a result of the response analysis up to that point, when further proceeding with the next diagnosis, the results is NO in an analysis result determination procedure (S27), so that the procedure goes back to the instruction presentation procedure (S20), and proceeds with the subsequent diagnosis program. When the results is YES in the analysis result determination procedure (S27), this means that diagnosis results are obtained, so that in a diagnosis output procedure (S28), the estimated disease or related data are output to a printer or display for the diagnostician and thus diagnosis ends.

The stimulus sentences, response sentences, disease database that are used here are the same as those described in Embodiment 1.

Embodiment 8

In the case of diagnosis of a person with hearing impairment, if the person has a poor sensitivity to a certain frequency band, the frequency characteristics that compensate for a reduction in the sensitivity to that frequency can be provided to the frequency characteristics of each band filter. In FIG. 1, the sound signals of all of the four frequency bands are replaced by frequency band noise signals, but sound signals of a part of the frequency bands are not supplied to the multiplying portion 3 but supplied directly to the adder 6, so that sound signal components can be left. Also with respect to each of the frequency bands whose sound signal components are to be left, a correction corresponding to degradation of the dynamic range or the frequency characteristics of hearing disorder may be performed.

In all of the above-described embodiments, the number of the band filters of the band filtering portions 1 and 2 is 4 as a typical example. However, the number thereof is not limited to 4 and can be 4 or less or more. The number of the frequency bands that is suitable, depending on the situation, can be used.

A recording medium on which a program for a procedure for a diagnostic method of the present invention is recorded includes ROM, RAM, flexible disks, CD-ROM, DVD, memory cards, hard disk on which the program is recorded. Furthermore, the medium includes communication media such as telephone networks, and transmission paths. A CD-ROM that stores the program of the diagnostic method of the present invention or a CD-ROM that stores disease database is mounted on a personal computer, so that the personal computer can be a diagnostic device of the present invention. Furthermore, the program of the diagnostic method of the present invention is downloaded into a personal computer through a telephone network or the like, the response collection results are sent to a remote disease database center and the determination results of the disease may be obtained from the center and output.

INDUSTRIAL APPLICABILITY

The present invention relates to a diagnostic device and a diagnostic method that employ Noise-Vocoded Speech Sound obtained by subjecting at least one frequency band signal of a sound signal to noise and. In particular, the present invention relates to diagnostic devices and diagnostic methods suitable to diagnose a disorder of people who may have a neural disorder.

The invention claimed is:

1. A diagnostic method comprising:
outputting a Noise-Vocoded Speech Sound signal that is obtained by dividing at least one portion of a sound signal into a frequency band signal and subjecting the frequency band signal to noise;
receiving a response of a patient; and
diagnosing a disease of the patient based on the response;
wherein the Noise-Vocoded Speech Sound signal is a word or a sentence in which a component of a sound source signal is subjected to noise is generated by:
extracting a frequency band signal with a predetermined frequency band from at least one portion of the sound signal by a first band filtering procedure having a plurality band filtering procedures;
extracting an amplitude envelope of each frequency signal by an envelope extracting procedure;
generating a frequency band noise signal corresponding to the predetermined frequency band from a noise source signal by a second band filtering procedure having a plurality of band filtering procedures;
multiplying the amplitude envelope of each frequency signal by the frequency band noise signal in a multiplying procedure; and
accumulating outputs obtained by the multiplying procedure in an adding procedure.

2. The diagnostic method according to claim 1, wherein a disease is estimated with reference to disease database, based on information corresponding to the output Noise Vocoded Speech Sound signal and the response.

3. The diagnostic method according to claim 1, wherein at least one of a number of the band filtering procedures for division into frequency band signals and a frequency of a frequency band boundary can be changed, at least depending on the language.

4. The diagnostic method according to claim 1, wherein at least one of a number of the band filtering procedures for division into frequency band signals and a frequency of a frequency band boundary can be changed through automatic language recognition.

5. The diagnostic method according to claim 1, comprising a sound signal extracting procedure for extracting only a sound component from a sound signal, wherein the Noise Vocoded Speech Sound signal is obtained by converting at least one portion of the extracted sound component to a Noise Vocoded Speech Sound signal.

6. A diagnostic device for executing the method according to claim 1.

7. A diagnostic method comprising:
outputting a Noise-Vocoded Speech Sound signal that is obtained by dividing at least one portion of a sound signal into a plurality of frequency band signals and subjecting the frequency band signals to noise;
receiving a response of a patient; and
diagnosing a disease of the patient based on the response;
wherein the Noise-Vocoded Speech Sound signal is a word or a sentence in which a component of a sound source is subjected to noise is generated by:
extracting a frequency band signal with a predetermined frequency band from at least one portion of the sound signal by a first band filtering procedure having a plurality band filtering procedures;
extracting an amplitude envelope of each frequency signal by an envelope extracting procedure;
generating a frequency band noise signal corresponding to the predetermined frequency band from a noise source signal by a second band filtering procedure having a plurality of band filtering procedures;
multiplying the amplitude envelope of each frequency signal by the frequency band noise signal in a multiplying procedure; and
accumulating outputs obtained by the multiplying procedure in an adding procedure.

8. The diagnostic method according to claim 7, wherein a disease is estimated with reference to disease database, based on information corresponding to the output Noise Vocoded Speech Sound signal and the response.

9. A diagnostic device for executing the method according to claim 7.

* * * * *